(12) United States Patent
Ohshita et al.

(10) Patent No.: US 8,039,499 B2
(45) Date of Patent: Oct. 18, 2011

(54) ESTER COMPOUND AND ITS USE

(75) Inventors: Jun Ohshita, Kobe (JP); Toru Uekawa, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 355 days.

(21) Appl. No.: 12/440,729

(22) PCT Filed: Aug. 24, 2007

(86) PCT No.: PCT/JP2007/066962
§ 371 (c)(1),
(2), (4) Date: Mar. 11, 2009

(87) PCT Pub. No.: WO2008/032585
PCT Pub. Date: Mar. 20, 2008

(65) Prior Publication Data
US 2009/0253763 A1      Oct. 8, 2009

(30) Foreign Application Priority Data

Sep. 15, 2006   (JP) .................... 2006-250505

(51) Int. Cl.
*A61K 31/4166* (2006.01)
*C07D 233/72* (2006.01)

(52) U.S. Cl. .................... 514/389; 548/317.1
(58) Field of Classification Search ........... 548/317.1; 514/389
See application file for complete search history.

(56) References Cited

U.S. PATENT DOCUMENTS

| | | | |
|---|---|---|---|
| 4,176,189 A * | 11/1979 | Itaya et al. ............ | 514/389 |
| 4,879,302 A | 11/1989 | Tessier et al. | |
| 2001/0049389 A1 | 12/2001 | Kubota et al. | |

FOREIGN PATENT DOCUMENTS

| | | |
|---|---|---|
| EP | 0267105 A2 | 5/1988 |
| JP | 51125739 A | 11/1976 |
| JP | 53086032 A | 7/1978 |

OTHER PUBLICATIONS

Office Action Issued Feb. 11, 2011 in CN Application. Ser. No. 2007800339201.
Zhang Yulei et. al."Preparation of S-HMPC by Combination of Enzyme Resolution and Chemical Transformation," Shanghai Chemical Engineering, vol. 24, No. 10, pp. 7-8, (1999).
Hu Zhiqiang, et. al.,"Progress of Pyrethroids Insecticides," Journal of Qingdao Institute of Chemical Technology, vol. 23, No. 1, pp. 48-51, (2002).
Jean Tessier,"Structure, Synthesis and Property of Deltamethrin," Translated Articles about Pesticides, vol. 5, No. 4, pp. 44-51, (1983).

* cited by examiner

*Primary Examiner* — Joseph K. McKane
*Assistant Examiner* — Janet L Coppins
(74) *Attorney, Agent, or Firm* — Panitch Schwarze Belisario & Nadel LLP

(57) ABSTRACT

An ester compound represented by the formula (I):

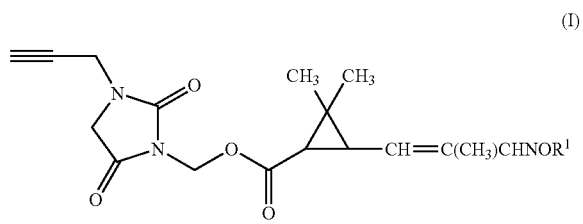

(I)

(wherein, $R^1$ represents a C1-C3 alkyl group, a 2-propenyl group or a 2-propynyl group.)
has excellent pest controlling activity and is useful as an active ingredient for a pest controlling agent.

12 Claims, No Drawings

ESTER COMPOUND AND ITS USE

CROSS-REFERENCE TO RELATED APPLICATION

This application is a Section 371 of International Application No. PCT/JP2007/066962, filed Aug. 24, 2007, which was published in the English language on Mar. 20, 2008 under International Publication No. WO 2008/032585 A1, and the disclosure of which is incorporated herein by reference.

TECHNICAL FIELD

The present invention relates to an ester compound and its use.

BACKGROUND ART

U.S. Pat. No. 4,176,189 describes that a certain kind of carboxylate compound of hydroxymethylimidazolidine-2,4-dione has insecticidal and acaricidal activity.

DISCLOSURE OF THE INVENTION

As a result of intensive study to find a compound having excellent pest controlling activity, the present inventor has found that a compound represented by the formula (I) described below has excellent pest controlling activity, and has completed the present invention.

That is, the present invention provides an ester compound represented by the formula (I):

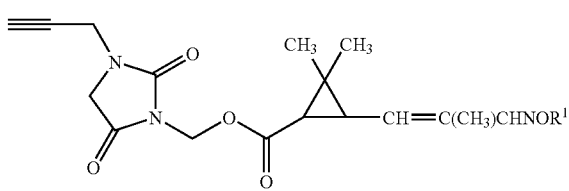

(I)

(wherein, $R^1$ represents a C1-C3 alkyl group, a 2-propenyl group or a 2-propynyl group.)
(hereinafter, referred to as the present compound), a pest controlling agent comprising the present compound as an active ingredient, and a method for controlling pests comprising applying the present compound to pests or a place where pests inhabit.

MODE OF CARRYING OUT THE INVENTION

In the present invention, examples of the C1-C3 alkyl group include a methyl group, an ethyl group, a 1-propyl group and a 2-propyl group.

There are isomers of the present compound, resulted from asymmetric carbon atoms present on the cyclopropane ring, and from the double bond, and the present invention includes each active isomer and a mixture of the isomers at any active ratio thereof.

Examples of the present compound include those described below:
a compound of the formula (I) in which the absolute configuration of 1-position on the cyclopropane ring is the R-configuration;
a compound of the formula (I) in which the relative configuration of the substituents at 1-position and at 3-position of the cyclopropane ring is the trans configuration;
a compound of the formula (I) in which the relative configuration of the substituents at 1-position and at 3-position of the cyclopropane ring is the cis configuration;
a compound of the formula (I) in which the relative configuration of the carbon-carbon double bond present in the substituent at 3-position of the cyclopropane ring is the E-configuration;
a compound of the formula (I) in which the absolute configuration of 1-position on the cyclopropane ring is the R-configuration and the relative configuration of the substituents at 1-position and at 3-position of the cyclopropane ring is the trans configuration;
a compound of the formula (I) in which the absolute configuration of 1-position on the cyclopropane ring is the R-configuration and the relative configuration of the substituents at 1-position and at 3-position of the cyclopropane ring is the cis configuration;
a compound of the formula (I) in which the absolute configuration of 1-position on the cyclopropane ring is the R-configuration, the relative configuration of the substituents at 1-position and at 3-position of the cyclopropane ring is the trans configuration and the relative configuration of the carbon-carbon double bond present in the substituent at 3-position of the cyclopropane ring is the E-configuration;
a compound of the formula (I) rich in an isomer in which the absolute configuration of 1-position on the cyclopropane ring is the R-configuration and the relative configuration of the substituents at 1-position and at 3-position of the cyclopropane ring is the trans configuration;
a compound of the formula (I) containing 80% or more of an isomer in which the absolute configuration of 1-position on the cyclopropane ring is the R-configuration and the relative configuration of the substituents at 1-position and at 3-position of the cyclopropane ring is the trans configuration;
a compound of the formula (I) containing 90% or more of an isomer in which the absolute configuration of 1-position on the cyclopropane ring is the R-configuration and the relative configuration of the substituents at 1-position and at 3-position of the cyclopropane ring is the trans configuration;
a compound of the formula (I) in which $R^1$ is a C1-C3 alkyl group and the absolute configuration of 1-position on the cyclopropane ring is the R-configuration;
a compound of the formula (I) in which $R^1$ is a C1-C3 alkyl group and the relative configuration of the substituents at 1-position and at 3-position of the cyclopropane ring is the trans configuration;
a compound of the formula (I) in which $R^1$ is a C1-C3 alkyl group and the relative configuration of the substituents at 1-position and at 3-position of the cyclopropane ring is the cis configuration;
a compound of the formula (I) in which $R^1$ is a C1-C3 alkyl group and the relative configuration of the carbon-carbon double bond present in the substituent at 3-position of the cyclopropane ring is the E-configuration;
a compound of the formula (I) in which $R^1$ is a C1-C3 alkyl group, the absolute configuration of 1-position on the cyclopropane ring is the R-configuration and the relative configuration of the substituents at 1-position and at 3-position of the cyclopropane ring is the trans configuration;
a compound of the formula (I) in which $R^1$ is a C1-C3 alkyl group, the absolute configuration of 1-position on the cyclopropane ring is the R-configuration and the relative configuration of the substituents at 1-position and at 3-position of the cyclopropane ring is the cis configuration;

a compound of the formula (I) in which $R^1$ is a C1-C3 alkyl group, the absolute configuration of 1-position on the cyclopropane ring is the R-configuration, the relative configuration of the substituents at 1-position and at 3-position of the cyclopropane ring is the trans configuration and the relative configuration of the carbon-carbon double bond present in the substituent at 3-position of the cyclopropane ring is the E-configuration;

a compound of the formula (I) rich in an isomer in which $R^1$ is a C1-C3 alkyl group, the absolute configuration of 1-position on the cyclopropane ring is the R-configuration and the relative configuration of the substituents at 1-position and at 3-position of the cyclopropane ring is the trans configuration;

a compound of the formula (I) containing 80% or more of an isomer in which $R^1$ is a C1-C3 alkyl group, the absolute configuration of 1-position on the cyclopropane ring is the R-configuration and the relative configuration of the substituents at 1-position and at 3-position of the cyclopropane ring is the trans configuration; and a compound of the formula (I) containing 90% or more of an isomer in which $R^1$ is a C1-C3 alkyl group, the absolute configuration of 1-position on the cyclopropane ring is the R-configuration and the relative configuration of the substituents at 1-position and at 3-position of the cyclopropane ring is the trans configuration.

Production Method

The present compound can be produced, for example, by a method shown below.

A method comprising a reaction of an alcohol compound represented by the formula (II):

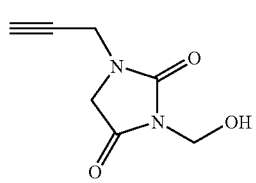

(II)

with a carboxylic acid compound represented by the formula (III):

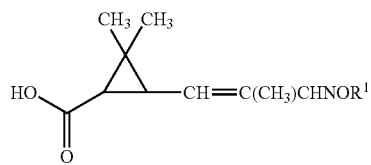

(III)

(wherein, $R^1$ represents the same meaning as described above.),
or a reactive derivative thereof (acid halide, acid anhydride and the like).

This reaction is carried out in a solvent in the presence of a condensing agent or a base.

Examples of the condensing agent include dicyclohexylcarbodiimide and 1-ethyl-3-(3-dimethylaminopropyl) carbodiimide hydrochloride.

Examples of the base include basic nitrogen-containing compounds such as triethylamine, pyridine, N,N-diethylaniline, 4-dimethylaminopyridine, diisopropylethylamine, etc.

Examples of the solvent include hydrocarbons such as benzene, toluene, hexane, etc.; ethers such as diethyl ether, tetrahydrofuran, etc.; halogenated hydrocarbons such as dichloromethane, 1,2-dichloroethane, chlorobenzene, etc.; and the like.

The reaction time is usually within the range of 5 minutes to 72 hours.

The reaction temperature is usually within the range of −20° C. to 100° C. (provided that, when a solvent used has a boiling point below 100° C., −20° C. to the boiling point of the solvent) preferably −5° C. to 100° C. (provided that, when a solvent used has a boiling point below 100° C., −5° C. to the boiling point of the solvent).

The reaction can be carried out at any molar ratio of the alcohol compound of the formula (II) to the carboxylic acid compound of the formula (III) or a reactive derivative thereof, but preferably at a ratio of one mole to one mole or around this ratio, for example, at a ratio of 0.5 to 2 moles of the carboxylic acid compound of the formula (III) or a reactive derivative thereof relative to one mole of the alcohol compound of the formula (II).

The condensing agent or the base can be used in any ratio usually in the range of one mole to an excess amount, preferably one to three moles, relative to one mole of the alcohol compound of the formula (II). The condensing agent or the base is appropriately selected depending on the kind of the carboxylic acid compound of the formula (III) or a reactive derivative thereof to be subjected to the reaction.

After the reaction has been completed, the present compound can be isolated by carrying out a conventional post-treatment operation such as pouring a reaction mixture into water, followed by extracting with an organic solvent and concentrating the extract. The isolated present compound can be further purified by chromatography, distillation, or the like.

The alcohol compound of the formula (II) is described, for example, in U.S. Pat. No. 5,350,859, and can be produced according to the method described therein.

Reference Production Method 1

A carboxylic acid compound represented by the formula (III) can be produced, for example, by hydrolysis of a compound represented by the formula (IV):

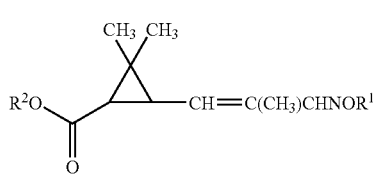

(IV)

(wherein, $R^2$ represents a methyl group, an ethyl group or a 1,1-dimethylethyl group (hereinafter, referred to as t-butyl group), and $R^1$ represents the same meaning as described above.) according to a method described in Shin Jikken Kagaku Koza vol. 14 II (1977, Maruzen Co., Ltd.), pp. 930 to 941.

A compound represented by the formula (IV) can be produced by a method described in Reference Production Method 2 or Reference Production Method 3.

Reference Production Method 2

A method of condensation of an aldehyde compound represented by the formula (V):

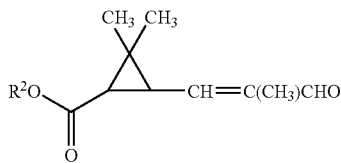

(wherein, $R^2$ represents the same meaning as described above.) with an amine compound represented by the formula (VI):

$R^1ONH_2$ (VI)

(wherein, $R^1$ represents the same meaning as described above.) or its proton acid salt.

The reaction is carried out usually in a solvent if necessary in the presence of a base.

Example of the base to be used if necessary include basic nitrogen-containing compounds such as triethylamine, pyridine, N,N-diethylaniline, 4-dimethylaminopyridine, diisopropylethylamine, etc.; alkali metal alkoxides such as sodium methoxide, etc.; organic bases such as organic acid salts such as sodium acetate, etc.; and inorganic bases such as sodium hydroxide, potassium carbonate, etc.

Examples of the solvent include hydrocarbons such as benzene, toluene, hexane, etc.; ethers such as diethyl ether, tetrahydrofuran, etc.; halogenated hydrocarbons such as dichloromethane, 1,2-dichloroethane, chloroform, chlorobenzene, etc.; and nitrogen-containing aromatic compounds such as pyridine, etc.

The reaction temperature of the reaction is usually within the range of –20° C. to 100° C. (provided that, when a solvent used has a boiling point below 100° C., –20° C. to the boiling point of the solvent), preferably –5° C. to 100° C. (provided that, when a solvent used has a boiling point below 100° C., –5° C. to the boiling point of the solvent), and the reaction time is usually within the range of 5 minutes to 72 hours.

The reaction can be carried out at any molar ratio of the aldehyde compound of the formula (V) to the amine compound of the formula (VI) or its protonic acid salt, but preferably at a ratio of one mole to one mole or around this ratio, for example, at a ratio of 1 to 3 moles of the amine compound of the formula (VI) or its protonic acid salt to one mole of the aldehyde compound of the formula (V).

The base to be used if necessary can be used in any ratio usually in the range of one mole to an excess amount, preferably one to three moles, relative to one mole of the amine compound of the formula (VI) or its protonic acid salt.

Examples of the protonic acid salt of the amine compound represented by the formula (VI) include hydrochlorides and sulfate salts.

After the reaction has been completed, the compound represented by the formula (IV) can be isolated by carrying out a conventional post-treatment operation such as pouring a reaction mixture into water, followed by extracting with an organic solvent and concentrating the extract. The isolated compound represented by the formula (IV) can be further purified by chromatography, distillation, re-crystallization or the like.

The aldehyde compound of the formula (V) is described, for example, in JP-A No. 2005-306859, and can be produced according to the method described therein.

Reference Production Method 3

A method of reaction of a hydroxyimine compound represented by the formula (VII):

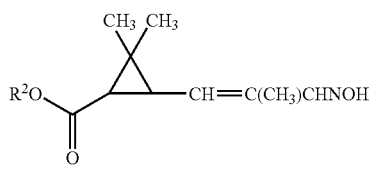

(wherein, $R^2$ represents the same meaning as described above.) with a compound represented by the formula (VIII):

$R^1$-L (VIII)

(wherein, L represents a leaving group such as a halogen atom, methanesulfonyloxy group, trifluoromethanesulfonyloxy group, p-toluenesulfonyloxy group and the like; and $R^1$ represents the same meaning as described above.).

The reaction is carried out usually in a solvent in the presence of a base.

Example of the base include basic nitrogen-containing compounds such as triethylamine, pyridine, N,N-diethylaniline, 4-dimethylaminopyridine, diisopropylethylamine, etc.; alkali metal alkoxides such as sodium methoxide, etc.; organic bases such as organic acid salts such as sodium acetate, etc.; and inorganic bases such as sodium hydroxide, potassium carbonate, sodium hydride, etc.

Examples of the solvent include hydrocarbons such as benzene, toluene, hexane, etc.; ethers such as diethyl ether, tetrahydrofuran, etc.; halogenated hydrocarbons such as dichloromethane, 1,2-dichloroethane, chloroform, chlorobenzene, etc.; amides such as dimethylformamide, etc.; and alcohols such as methanol, ethanol, etc.

The reaction temperature of the reaction is usually within the range of –20° C. to 100° C. (provided that, when a solvent used has a boiling point below 100° C., –20° C. to the boiling point of the solvent), preferably –5° C. to 100° C. (provided that, when a solvent used has a boiling point below 100° C., –5° C. to the boiling point of the solvent), and the reaction time is usually within the range of 5 minutes to 72 hours.

The reaction can be carried out at any molar ratio of the hydroxyimine compound of the formula (VII) to the compound of the formula (VIII), but preferably at a ratio of one mole to one mole or around this ratio, for example, at a ratio of 1 to 3 moles of the compound of the formula (VIII) to one mole of the hydroxyimine compound of the formula (VII).

The base can be used in any ratio usually in the range of one mole to an excess amount, preferably one to three moles, relative to one mole of the hydroxyimine compound of the formula (VII).

After the reaction has been completed, the ester compound represented by the formula (IV) can be isolated by carrying out a conventional post-treatment operation such as pouring a reaction mixture into water, followed by extracting with an organic solvent and concentrating the extract. The isolated ester compound represented by the formula (IV) can be further purified by chromatography, distillation, re-crystallization or the like.

The hydroxyimine compound represented by the formula (VII) can be produced by using a hydroxylamine or its proton acid salt instead of the amine compound represented by the formula (VI) or its protonic acid salt in Reference Production Method 2.

Examples of pests controlled by the present compound include arthropods such as insects, acarines, and the like. Specific examples are those described below.

Lepidoptera:

Pyralid moths (Pyralidae) such as rice stem borer (*Chilo suppressalis*), rice leafroller (*Cnaphalocrocis medinalis*), Indian meal moth (*Plodia interpunctella*), and the like, owlet moths (Noctuidae) such as common cutworm (*Spodoptera litura*), rice armyworm (*Pseudaletia separata*), cabbage armyworm (*Mamestra brassicae*), and the like, whites (Pieridae) such as common cabbageworm (*Pieris rapae*), and the like, tortricid moths (Tortricidae) such as *Adoxophyes orana*, and the like, Carposinidae, lyonetiid moths (Lyonetiidae), tussock moths (Lymantriidae), *Autographa, Agrotis* spp. such as cutworm (*Agrotis segetum*), black cutworm (*Agrotis ipsilon*), and the like, *Helicoverpa* spp., *Heliothis* spp., diamondback (*Plutella xylostella*), rice skipper (*Parnara guttata*), casemaking clothes moth (*Tinea pellionella*), webbing clothes moth (*Tineola bisselliella*), and the like;

Diptera:

Mosquitos (Calicidae) such as common mosquito (*Culex pipiens pallens*), *Culex tritaeniorhynchus*, and the like, *Aedes* spp. such as *Aedes aegypti, Aedes albopictus*, and the like, *Anopheles* such as *Anopheles sinensis* and the like, midges (Chironomidae), house flies (Muscidae) such as housefly (*Musca domestica*), false stablefly (*Muscina stabulans*), lesser housefly (*Fannia canicularis*), and the like, Calliphoridae, Sarcophagidae, anthomyiid flies (Anthomyiidae) such as seedcorn maggot (*Hylemya platura*), onion maggot (*Delia antiqua*), and the like, fruit flies (Tephritidae), small fruit flies (Drosophilidae), moth flies (Psychodidae), Phoridae, black flies (Simuliidae), Tabanidae, stable flies (Stomoxyidae), Ceratopogonidae, and the like;

Blattodea:

German cockroach (*Blattella germanica*), smokybrown cockroach (*Periplaneta fuliginosa*), American cockroach (*Periplaneta americana*), brown cockroach (*Periplaneta brunnea*), oriental cockroach (*Blatta orientalis*) and the like;

Hymenoptera:

Ants (Formicidae), hornets, yellow jackets and potter wasps (Vespidae), bethylid wasps, sawflies (Tenthredinidae) such as cabbage sawfly (Athalia rosae japonensis), and the like;

Aphaniptera:

*Ctenocephalides canis, Ctenocephalides felis, Pulex irritans* and the like;

Anoplura:

*Pediculus humanus, Phthirus pubis, Pediculus humanus humanus, Pediculus humanus corporis*, and the like;

Isoptera:

*Reticulitermes speratus, Coptotermes formosanus*, and the like;

Hemiptera:

Planthoppers (Delphacidae) such as small brown planthopper (*Laodelphax striatellus*), brown rice planthopper (*Nilaparvata lugens*), white-backed rice planthopper (*Sogatella furcifera*), and the like, leafhoppers (Deltocephalidae) such as green rice leafhopper (*Nephotettix cincticeps*), green rice leafhopper (*Nephotettix virescens*), and the like, aphids (Aphididae), stink bugs (Pentatomidae), whiteflies (Aleyrodidae), scales (Coccidae), lace bugs (Tingidae), psyllids (Psyllidae), and the like;

Coleoptera:

Corn rootworm (Diabrotica spp.) such as *Attagenus japonicus, Anthrenus verbasci*, western corn rootworm (*Diabrotica virgifera*), southern corn rootworm (*Diabrotica undecimpunctata howardi*), and the like, scarabs (Scarabaeidae) such as cupreous chafer (*Anomala cuprea*), soybeen beetle (*Anomala rufocuprea*), and the like, weevils (Curculionidae) such as maize weevil (*Sitophilus zeamais*), rice water weevil (*Lissorhoptrus oryzophilus*), cottonseed weevil (*Anthonomus gradis gradis*), adzuki been weevil (*Callosobruchuys chienensis*), and the like, darkling beetles (Tenebrionidae) such as yellow mealworm (*Tenebrio inolitor*), red flour beetle (*Tribolium castaneum*), and the like, leaf beetles (Chrysomelidae) such as rice leaf beetle (*Oulema oryzae*), striped flea beetle (*Phyllotreta striolata*), cucurbit leaf beetle (*Aulacophora femoralis*), and the like, drugstore beetles (Anobiidae), *Epilachna* spp. such as twenty-eight-spotted ladybird (*Epilachna vigintioctopunctata*), and the like, powder post beetles (Lyctidae), false powder post beetles (Bostrychidae), longhorn beetles (Cerambycidae), rove beetle (*Paederus fuscipes*), and the like;

Thysanoptera:

*Thrips palmi, Frankliniella occidentalis*, flower thrips (*Thrips hawaiiensis*), and the like;

Orthoptera:

Mole crickets (Gryllotalpidae), grasshoppers (Acrididae), and the like;

Acarina:

House dust mites (Epidermoptidae) such as *Dermatophagoides farinae, Dermatophagoides ptrenyssnus*, and the like, acarid mites (Acaridae) such as mold mite (*Tyrophagus putrescentiae*), brown legged grain mite (*Aleuroglyphus ovatus*), and the like, Glycyphagidae such as *Glycyphagus privatus, Glycyphagus domesticus*, groceries mite (*Glycyphagus destructor*), and the like, cheyletid mites (Cheyletidae) such as *Cheyletus malaccensis, Cheyletus fortis*, and the like, Tarsonemidae, Chortoglyphidae, Haplochthoniidae, spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and the like; and hard ticks (Ixodidae) such as *Haemaphysalis longicornis*, and the like.

The pest controlling agent of the present invention may be the present compound itself or, usually, may be a formulation comprising the present compound and an inert carrier.

Examples of the formulation include oil solutions, emulsifiable concentrates, wettable powders, flowable formulations (e.g. aqueous suspension and aqueous emulsion), dusts, granules, aerosols, volatile formulations by heating (e.g. mosquito-coil, mosquito-mat for electric heating and volatile formulations with absorptive wick for heating), heating fumigants (e.g. self-burning type fumigants, chemical reaction type fumigants and porous ceramic plate fumigant), non-heating volatile formulations (e.g. resin volatile formulations and impregnated paper volatile formulations), smoking formulations (e.g. fogging), ULV formulations and poisonous baits.

The formulation can be prepared, for example, by the following methods:

(1) A method of mixing the present compound with a solid carrier, liquid carrier, gaseous carrier, bait or the like, optionally adding auxiliaries for formulation such as surfactants and the like, and formulating the mixture;

(2) A method of impregnating a base material containing no active ingredients with the present compound; and (3) A method of mixing the present compound with a base material and forming the mixture.

These formulations usually contain 0.001 to 95% by weight of the present compound, depending on the type of formulations.

Examples of the carrier used for the formulation include solid carriers such as clays (e.g. kaolin clay, diatomaceous earth, synthetic hydrated silicon oxide, bentonite, Fubasami clay and acid clay), talc and the like, ceramics, other inorganic minerals (e.g. sericite, quartz, sulfur, active carbon, calcium carbonate, hydrated silicon oxide and montmorillonite) and chemical fertilizers (e.g. ammonium sulfate, ammonium phosphate, ammonium nitrate, urea and ammonium chloride); liquid carriers such as water, alcohols (e.g. methanol and ethanol), ketones (e.g. acetone and methyl ethyl ketone), aromatic hydrocarbons (e.g. benzene, toluene, xylene, ethylbenzene, methylnaphthalene and phenylxylylethane), aliphatic hydrocarbons (e.g. hexane, cyclohexane, kerosene and gas oil), esters (e.g. ethyl acetate and butyl acetate), nitriles (e.g. acetonitrile and isobutyronitrile), ethers (e.g. diisopropyl ether and dioxane), acid amides (e.g. N,N-dimethylformamide and N,N-dimethylacetamide), halogenated hydrocarbons (dichloromethane, trichloroethane and carbon tetrachloride), dimethyl sulfoxide and vegetable oils (e.g. soybean oil and cottonseed oil); and gaseous carriers such as chlorofluorocarbon gas, butane gas, LPG (liquefied petroleum gas), dimethyl ether and carbon dioxide gas.

Examples of the surfactant include alkyl sulfate esters, alkylsulfonate salts, alkylarylsulfonate salts, alkyl aryl ethers, polyoxyethylenated alkyl aryl ethers, polyethylene glycol ethers, polyhydric alcohol esters and sugar alcohol derivatives.

Examples of the other auxiliaries for a formulation include sticking agents, dispersing agents and stabilizers, typically casein, gelatin, polysaccharides (e.g. starch, gum arabic, cellulose derivatives and alginic acid), lignin derivatives, bentonite, synthetic water-soluble polymers (e.g. polyvinyl alcohol and polyvinylpyrrolidone), polyacrylic acid, BHT (2,6-di-t-butyl-4-methyphenol) and BHA (mixture of 2-t-butyl-4-methoxyphenol and 3-t-butyl-4-methoxyphenol).

Examples of the solid carrier for a mosquito-coil include a mixture of raw plant powder such as wood powder and Pyrethrum marc and a binding agent such as Tabu powder (powder of Machilus thunbergii), starch or gluten.

Examples of the shaped solid carrier for a mosquito-mat for electric heating include plates of compacted fibrils of cotton linters and of a mixture of pulp and cotton linters.

Examples of the solid carrier for the self-burning type fumigant includes exothermic combustion agents such as nitrate, nitrite, guanidine salt, potassium chlorate, nitrocellulose, ethylcellulose and wood powder, pyrolytic stimulating agents such as alkali metal salts, alkaline earth metal salts, dichromates and chromates, oxygen sources such as potassium nitrate, combustion assistants such as melanin and wheat starch, bulk fillers such as diatomaceous earth and binding agents such as synthetic glue.

Examples of the solid carrier for a chemical reaction type fumigant include exothermic agents such as alkali metal sulfides, polysulfides, hydrogensulfides and calcium oxide, catalytic agents such as carbonaceous substances, iron carbide and activated clay, organic foaming agents such as azodicarbonamide, benzenesulfonyl hydrazide, dinitrosopentamethylene tetramine, polystyrene and polyurethane and fillers such as natural and synthetic fibers.

Examples of the solid carrier for a non-heating volatile formulation include thermoplastic resins and paper such as filter paper and Japanese paper.

Examples of the base material for a poisonous bait include bait ingredients such as grain powder, vegetable oil, sugar and crystalline cellulose, antioxidants such as dibutyl hydroxytoluene and nordihydroguairetic acid, preservatives such as dehydroacetic acid, substances for preventing children and pets from erroneous eating such as red pepper powder, and pest-attractant flavorants such as cheese flavorant, onion flavorant and peanut oil.

The method for controlling pests of the present invention is usually carried out by applying the pest controlling agent of the present invention containing an effective amount of the present compound to pests or a place where pests inhabit.

The application methods of the pesticidal composition of the present invention are, for example, given below. The methods are suitably selected according to the type of the pesticidal composition or application places.

(1) A method applying the pesticidal composition of the present invention as it is to pests or a place where the pests inhabit.

(2) A method diluting the pesticadal composition of the present invention with a solvent such as water, and then spraying it to pests or a place where the pests inhabit. In that case, the pesticidal composition of the present invention formulated to emulsifiable concentrates, wettable powders, flowable formulations, microcapsule formulations and so on is diluted to make the concentration of the present compound to 0.1 to 10000 ppm.

(3) A method volatilizing an active ingredient by heating the pesticidal composition of the present invention at a place where pests inhabit. In that case, the dosage and concentration of the present compound are decided according to type of the pesticidal composition of the present invention, time, place and method of the application, kind of the pests, damage and so on.

The pest controlling agent of the present invention can be used together with or by mixing with other insecticides, nematocides, fungicides, herbicides, plant growth regulators, repellents, synergists, fertilizers and/or soil conditioners.

Examples of the active ingredients of the insecticide and acaricide include:

organophosphorus compounds such as fenitrothion, fenthion, diazinon, chlorpyrifos, acephate, methidathion, disulfoton, DDVP, sulprofos, cyanophos, dioxabenzofos, dimethoate, phenthoate, malathion, trichlorfon, azinphosmethyl, monocrotophos and ethion;

carbamate compounds such as BPMC, benfuracarb, propoxur, carbosulfan, carbaryl, methomyl, ethiofencarb, aldicarb, oxamyl and fenothiocarb;

pyrethroid compounds such as etofenprox, fenvalerate, esfenvalerate, fenpropathrin, cypermethrin, permethrin, cyhalothrin, deltamethrin, cycloprothrin, fluvalinate, bifenthrin, 2-methyl-2-(4-bromodifluoromethoxyphenyl) propyl (3-phenoxybenzyl)ether, tralomethrin, silafluofen, d-phenothrin, cyphenothrin, d-resmethrin, acrinathrin, cyfluthrin, tefluthrin, transfluthrin, tetramethrin, allethrin, d-furamethrin, prallethrin, empenthrin and 5-(2-propynyl) furfuryl 2,2,3,3-tetramethylcyclopropanecarboxylate;

nitroimidazolidine derivatives; N-cyanoamidine derivatives such as acetamiprid; chlorinated hydrocarbon compounds such as endosulfan, γ-BHC and 1,1-bis(chlorophenyl)-2,2,2-trichloroethanol; benzoylphenylurea compounds such as chlorfluazuron, teflubenzuron and flufenoxuron; phenylpyrazole compounds; metoxadiazon; bromopropylate; tetradifon; chinomethionat; pyridaben; fenpyroximate; diafenthiuron; tebufenpyrad; polynactins complex such as tetranactin, dinactin and trinactin; pyrimidifen; milbemectin; abamectin; ivermectin; and azadirachtin.

Examples of the repellent include 3,4-caranediol, N,N-diethyl-m-toluamide, 1-methylpropyl 2-(2-hydroxyethyl)-1-piperidinecarboxylate, p-menthan-3,8-diol, botanical essential oils such as hyssop oil, and the like.

Examples of the synergist include bis(2,3,3,3-tetrachloropropyl)ether (S-421), N-(2-ethylhexyl)bicyclo[2.2.1]hept-5-ene-2,3-dicarboximide (MGK-264) and 5-[2-(2-Butoxyethoxy)ethoxymethyl]-6-propyl-1,3-benzodioxole (piperonyl butoxide).

EXAMPLES

The present invention will be illustrated further in detail by the following Production Examples, Formulation Examples and Test Examples, but the present invention is not limited to these examples.

First, the Production Examples of the present compound will be described.

Production Example 1

Under nitrogen atmosphere, to a mixture of 0.25 g of 3-hydroxymethyl-1-(2-propynyl)imidazolidine-2,4-dione:

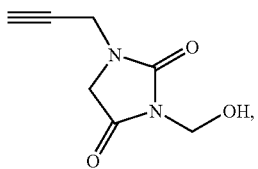

0.32 g of (1R)-trans-3-[(E)-3-methoxyimino-2-methyl-1-propenyl]-2,2-dimethylcyclopropanecarboxylic acid, catalytic amount of 4-dimethylaminopyridine and 5 ml of anhydrous tetrahydrofuran was added 0.30 g of 1-ethyl-3-(3-dimethylaminopropyl) carbodiimide hydrochloride and the mixture was stirred at room temperature overnight. Thereafter, saturated brine was added to the reaction mixture, and the mixture was extracted with ethyl acetate. The organic layer was washed with saturated brine, and dried over anhydrous magnesium sulfate, then, filtrated, and the filtrate was concentrated under reduced pressure. The residue was subjected to silica gel column chromatography to obtain 0.34 g of 2,5-dioxo-3-(2-propynyl)imidazolidin-1-ylmethyl (1R)-trans-3-[(E)-3-methoxyimino-2-methyl-1-propenyl]-2,2-dimethylcyclopropanecarboxylate (hereinafter, referred to as the present compound (1)) represented by the formula (1):

(1)

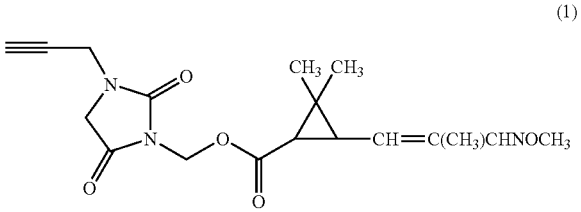

The present compound (1)
$^1$H-NMR (CDCl$_3$, TMS) δ (ppm): 7.62 (1H, s), 5.61 (1H, d), 5.49 (1H, d), 5.33 (1H, d), 4.27 (2H, d), 4.05 (2H, s), 3.87 (3H, s), 2.37 (1H, t), 2.26 (1H, dd), 1.91 (3H, d), 1.58 (1H, d), 1.31 (3H, s), 1.16 (3H, s)

Production Example 2

Under nitrogen atmosphere, to a mixture of 0.44 g of 3-hydroxymethyl-1-(2-propynyl)imidazolidine-2,4-dione, 0.58 g of (1R)-trans-3-[(E)-3-ethoxyimino-2-methyl-1-propenyl]-2,2-dimethylcyclopropanecarboxylic acid, catalytic amount of 4-dimethylaminopyridine and 5 ml of anhydrous chloroform was added 0.50 g of 1-ethyl-3-(3-dimethylaminopropyl) carbodiimide hydrochloride and the mixture was stirred at room temperature overnight. Thereafter, saturated brine was added to the reaction mixture, and the mixture was extracted with ethyl acetate. The organic layer was washed with saturated brine, and dried over anhydrous magnesium sulfate, then, filtrated, and the filtrate was concentrated under reduced pressure. The residue was subjected to silica gel column chromatography to obtain 0.34 g of 2,5-dioxo-3-(2-propynyl)imidazolidin-1-ylmethyl (1R)-trans-3-[(E)-3-ethoxyimino-2-methyl-1-propenyl]-2,2-dimethylcyclopropanecarboxylate (hereinafter, referred to as the present compound (2)) represented by the formula (2):

(2)

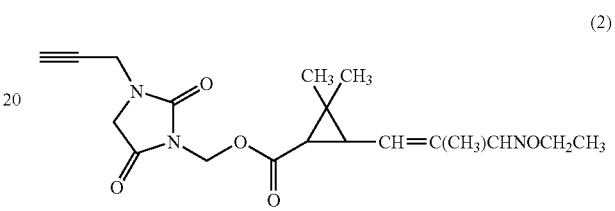

The present compound (2)
$^1$H-NMR (CDCl$_3$, TMS) δ (ppm): 7.63 (1H, s), 5.61 (1H, d), 5.49 (1H, d), 5.32 (1H, d), 4.27 (2H, d), 4.12 (2H, q), 4.05 (2H, s), 2.37 (1H, t), 2.26 (1H, dd), 1.91 (3H, d), 1.58 (1H, d), 1.31 (3H, s), 1.26 (3H, t), 1.15 (3H, s)

Production Example 3

Under nitrogen atmosphere, to a mixture of 0.17 g of 3-hydroxymethyl-1-(2-propynyl)imidazolidine-2,4-dione, 0.24 g of (1R)-trans-3-[(E)-3-(2-propenyloxyimino)-2-methyl-1-propenyl]-2,2-dimethylcyclopropanecarboxylic acid, catalytic amount of 4-dimethylaminopyridine and 3 ml of anhydrous chloroform was added 0.19 g of 1-ethyl-3-(3-dimethylaminopropyl)carbodiimide hydrochloride and the mixture was stirred at room temperature for 3 hours. Thereafter, saturated brine was added to the reaction mixture, and the mixture was extracted with ethyl acetate. The organic layer was washed with saturated brine, and dried over anhydrous magnesium sulfate, then, filtrated, and the filtrate was concentrated under reduced pressure. The residue was subjected to silica gel column chromatography to obtain 0.24 g of 2,5-dioxo-3-(2-propynyl)imidazolidin-1-ylmethyl (1R)-trans-3-[(E)-3-(2-propenyloxyimino)-2-methyl-1-propenyl]-2,2-dimethylcyclopropanecarboxylate (hereinafter, referred to as the present compound (3)) represented by the formula (3):

(3)

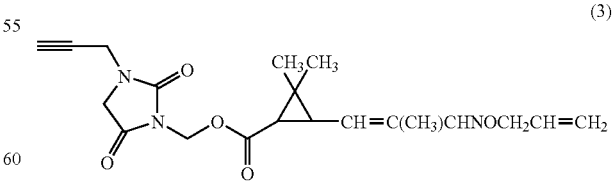

The present compound (3)
$^1$H-NMR (CDCl$_3$, TMS) δ (ppm): 7.67 (1H, s), 6.00 (1H, m), 5.61 (1H, d), 5.48 (1H, d), 5.34-5.20 (3H, m), 4.57 (2H, dt), 4.27 (2H, d), 4.05 (2H, s), 2.36 (1H, t), 2.26 (1H, dd), 1.90 (3H, d), 1.58 (1H, d), 1.31 (3H, s), 1.15 (3H, s)

Production Example 4

Under nitrogen atmosphere, to a mixture of 0.17 g of 3-hydroxymethyl-1-(2-propynyl)imidazolidine-2,4-dione, 0.25 g of (1R)-trans-2,2-dimethyl-3-[(E)-2-methyl-3-propoxyimino-1-propenyl]cyclopropanecarboxylic acid, catalytic amount of 4-dimethylaminopyridine and 3 ml of anhydrous chloroform was added 0.23 g of 1-ethyl-3-(3-dimethylaminopropyl)carbodiimide hydrochloride and the mixture was stirred at room temperature overnight. Thereafter, saturated brine was added to the reaction mixture, and the mixture was extracted with ethyl acetate. The organic layer was washed with saturated brine, and dried over anhydrous magnesium sulfate, then, filtrated, and the filtrate was concentrated under reduced pressure. The residue was subjected to silica gel column chromatography to obtain 0.20 g of 2,5-dioxo-3-(2-propynyl)imidazolidin-1-ylmethyl (1R)-trans-2,2-dimethyl-3-[(E)-2-methyl-3-propoxyimino-1-propenyl]cyclopropanecarboxylate (hereinafter, referred to as the present compound (4)) represented by the formula (4):

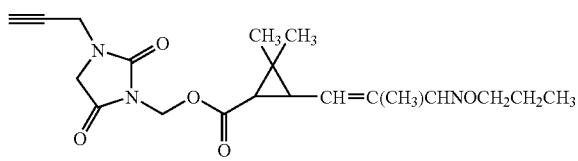

(4)

The present compound (4)

$^1$H-NMR (CDCl$_3$, TMS) δ (ppm): 7.64 (1H, s), 5.61 (1H, d), 5.48 (1H, d), 5.32 (1H, d), 4.27 (2H, d), 4.06-4.00 (4H, m), 2.37 (1H, t), 2.26 (1H, dd), 1.90 (3H, s), 1.72-1.62 (2H, m), 1.57 (1H, d), 1.31 (3H, s), 1.15 (3H, s), 0.94 (3H, t)

Production Example 5

Under nitrogen atmosphere, to a mixture of 0.17 g of 3-hydroxymethyl-1-(2-propynyl)imidazolidine-2,4-dione, 0.25 g of (1R)-trans-3-[(E)-3-isopropoxyimino-2-methyl-1-propenyl]-2,2-dimethylcyclopropanecarboxylic acid, catalytic amount of 4-dimethylaminopyridine and 5 ml of anhydrous chloroform was added 0.23 g of 1-ethyl-3-(3-dimethylaminopropyl)carbodiimide hydrochloride and the mixture was stirred at room temperature for 5 hours. Thereafter, saturated brine was added to the reaction mixture, and the mixture was extracted with ethyl acetate. The organic layer was washed with saturated brine, and dried over anhydrous magnesium sulfate, then, filtrated, and the filtrate was concentrated under reduced pressure. The residue was subjected to silica gel column chromatography to obtain 0.20 g of 2,5-dioxo-3-(2-propynyl)imidazolidin-1-ylmethyl (1R)-trans-3-[(E)-3-isopropoxyimino-2-methyl-1-propenyl]-2,2-dimethylcyclopropanecarboxylate (hereinafter, referred to as the present compound (5)) represented by the formula (5):

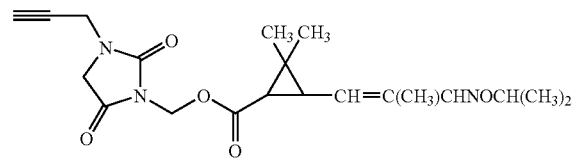

(5)

The present compound (5)

$^1$H-NMR (CDCl$_3$, TMS) δ (ppm): 7.61 (1H, s), 5.61 (1H, d), 5.48 (1H, d), 5.30 (1H, d), 4.34 (1H, m), 4.27 (2H, d), 4.05 (2H, s), 2.36 (1H, t), 2.26 (1H, dd), 1.91 (3H, d), 1.57 (1H, d), 1.31 (3H, s), 1.24 (6H, d), 1.15 (3H, s)

Production Example 6

Under nitrogen atmosphere, to a mixture of 0.12 g of 3-hydroxymethyl-1-(2-propynyl)imidazolidine-2,4-dione, 0.17 g of (1R)-trans-2,2-dimethyl-3-[(E)-2-methyl-3-(2-propynyloxyimino)-1-propenyl]cyclopropanecarboxylic acid, catalytic amount of 4-dimethylaminopyridine and 3 ml of anhydrous chloroform was added 0.16 g of 1-ethyl-3-(3-dimethylaminopropyl)carbodiimide hydrochloride and the mixture was stirred at room temperature overnight. Thereafter, saturated brine was added to the reaction mixture, and the mixture was extracted with ethyl acetate. The organic layer was washed with saturated brine, and dried over anhydrous magnesium sulfate, then, filtrated, and the filtrate was concentrated under reduced pressure. The residue was subjected to silica gel column chromatography to obtain 0.15 g of 2,5-dioxo-3-(2-propynyl)imidazolidin-1-ylmethyl (1R)-trans-2,2-dimethyl-3-[(E)-2-methyl-3-(2-propynyloxyimino)-1-propenyl]cyclopropanecarboxylate (hereinafter, referred to as the present compound (6)) represented by the formula (6):

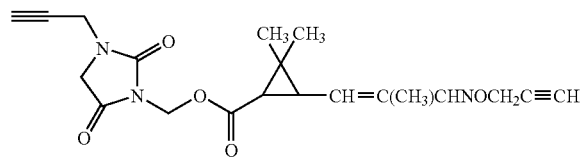

(6)

The present compound (6)

$^1$H-NMR (CDCl$_3$, TMS) δ (ppm): 7.67 (1H, s), 5.61 (1H, d), 5.49 (1H, d), 5.37 (1H, d), 4.67 (2H, d), 4.27 (2H, d), 4.05 (2H, s), 2.46 (1H, t), 2.37 (1H, t), 2.27 (1H, dd), 1.91 (3H, d), 1.59 (1H, d), 1.31 (3H, s), 1.16 (3H, s)

Next, Reference Production Examples of intermediates used in production of the present compounds will be shown.

Reference Production Example 1

Under nitrogen atmosphere, a mixture of 0.59 g of methyl (1R)-trans-2,2-dimethyl-3-[(E)-2-methyl-3-oxo-1-propenyl]cyclopropanecarboxylate:

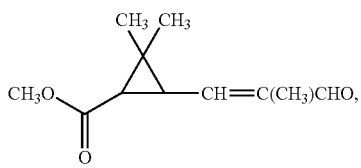

0.25 g of O-methylhydroxylamine hydrochloride and 2 ml of pyridine was stirred at room temperature for 5 hours. Then, ethyl acetate was added to the reaction mixture, and the mixture was washed with 1 mol/L hydrochloric acid and saturated brine respectively. The organic layer was dried over anhydrous magnesium sulfate, then, filtrated. The filtrate was concentrated under reduced pressure; to obtain 0.57 g of a crude product of methyl (1R)-trans-3-[(E)-3-methoxyimino-2-methyl-1-propenyl]-2,2-dimethylcyclopropanecarboxylate:

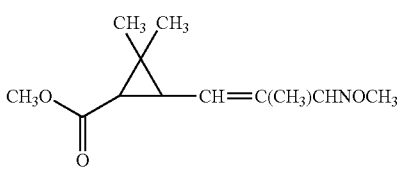

The product was subjected to Reference Production Example 2 without purification.

Reference Production Example 2

Under nitrogen atmosphere, a mixture of 0.57 g of methyl (1R)-trans-3-[(E)-3-methoxyimino-2-methyl-1-propenyl]-2,2-dimethylcyclopropanecarboxylate, 7.5 ml of 1 mol/L sodium hydroxide aqueous solution and 7.5 ml of methanol was stirred at 60° C. for 3 hours. Then, water was added to the reaction mixture, and the mixture was washed with diethyl ether. 1 mol/L hydrochloric acid was added to the resultant aqueous layer to make the layer acidic, and extraction with diethyl ether was performed, then, the organic layer was dried over anhydrous magnesium sulfate, then, filtrated. The filtrate was concentrated under reduced pressure, then, the residue was subjected to silica gel column chromatography to obtain 0.32 g of (1R)-trans-3-[(E)-3-methoxyimino-2-methyl-1-propenyl]-2,2-dimethylcyclopropanecarboxylic acid:

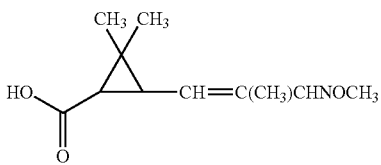

$^1$H-NMR (CDCl$_3$, TMS) δ (ppm): 7.64 (1H, s), 5.38 (1H, d), 3.88 (3H, s), 2.28 (1H, dd), 1.92 (3H, d), 1.61 (1H, d), 1.35 (3H, s), 1.20 (3H, s)

Reference Production Example 3

Under nitrogen atmosphere, a mixture of 0.94 g of methyl (1R)-trans-2,2-dimethyl-3-[(E)-2-methyl-3-oxo-1-propenyl]cyclopropanecarboxylate, 0.47 g of O-ethylhydroxylamine hydrochloride and 2 ml of pyridine was stirred at room temperature for 4 hours. Then, ethyl acetate was added to the reaction mixture, and the mixture was washed with 1 mol/L hydrochloric acid and saturated brine respectively. The organic layer was dried over anhydrous magnesium sulfate, then, filtrated, and the filtrate was concentrated under reduced pressure. The residue was subjected to silica gel column chromatography to obtain 0.92 g of methyl (1R)-trans-3-[(E)-3-ethoxyimino-2-methyl-1-propenyl]-2,2-dimethylcyclopropanecarboxylate:

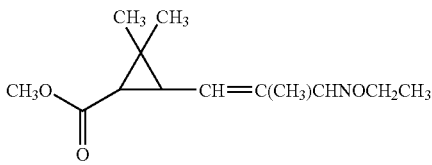

$^1$H-NMR (CDCl$_3$, TMS) δ (ppm): 7.65 (1H, s), 5.36 (1H, d), 4.12 (2H, q), 3.69 (3H, s), 2.25 (1H, dd), 1.92 (3H, s), 1.59 (1H, d), 1.30 (3H, s), 1.27 (3H, t), 1.17 (3H, s)

Reference Production Example 4

Under nitrogen atmosphere, a mixture of 0.56 g of methyl (1R)-trans-3-[(E)-3-ethoxyimino-2-methyl-1-propenyl]-2,2-dimethylcyclopropanecarboxylate, 6.9 ml of 1 mol/L sodium hydroxide aqueous solution and 6.9 ml of methanol was stirred at 60° C. for 2 hours. Then, water was added to the reaction mixture, and the mixture was washed with diethyl ether. 1 mol/L hydrochloric acid was added to the resultant aqueous layer to make the layer acidic, and extraction with diethyl ether was performed, then, the organic layer was dried over anhydrous magnesium sulfate, then, filtrated. The filtrate was concentrated under reduced pressure to obtain 0.58 g of a crude product of (1R)-trans-3-[(E)-3-ethoxyimino-2-methyl-1-propenyl]-2,2-dimethylcyclopropanecarboxylic acid:

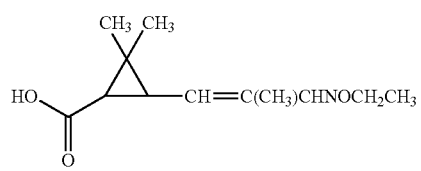

The product was subjected to Production Example 2 without purification.

Reference Production Example 5

Under nitrogen atmosphere, a mixture of 1.0 g of t-butyl (1R)-trans-3-formyl-2,2-dimethylcyclopropanecarboxylate:

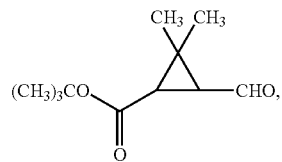

catalytic amount of pyrrolidine and 10 ml of toluene was heated at 60° C., and into this was added a mixture of 0.32 g of propionaldehyde and 5 ml of toluene dropwise over a period of 30 minutes, then, the mixture was stirred at 60° C. for 1 hour. The reaction mixture was cooled down to room temperature and saturated brine was added to the mixture which was extracted with ethyl acetate. The organic layer was washed with saturated brine, and dried over anhydrous magnesium sulfate, then, filtrated, and the filtrate was concentrated under reduced pressure. The residue was subjected to silica gel column chromatography to obtain 0.75 g of t-butyl (1R)-trans-2,2-dimethyl-3-[(E)-2-methyl-3-oxo-1-propenyl]cyclopropanecarboxylate:

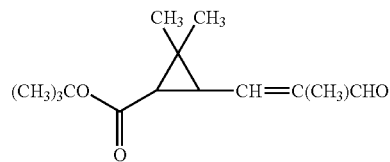

$^1$H-NMR (CDCl$_3$, TMS) δ (ppm): 9.36 (1H, s), 6.14 (1H, d), 2.31 (1H, dd), 1.86 (3H, d), 1.77 (1H, d), 1.47 (9H, s), 1.33 (3H, s), 1.27 (3H, s)

Reference Production Example 6

Under nitrogen atmosphere, a mixture of 0.75 g of t-butyl (1R)-trans-2,2-dimethyl-3-[(E)-2-methyl-3-oxo-1-propenyl]cyclopropanecarboxylate, 0.36 g of O-allylhydroxylamine hydrochloride and 2 ml of pyridine was stirred at room temperature for 4 hours. Then, ethyl acetate was added to the reaction mixture, and the mixture was washed with 1 mol/L hydrochloric acid and saturated brine respectively. The organic layer was dried over anhydrous magnesium sulfate, then, filtrated. The filtrate was concentrated under reduced pressure, to obtain 0.84 g of a crude product of t-butyl (1R)-trans-3-[(E)-3-(2-propenyloxyimino)-2-methyl-1-propenyl]-2,2-dimethylcyclopropanecarboxylate:

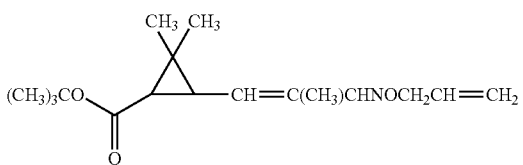

The product was subjected to Reference Production Example 7 without purification.

Reference Production Example 7

Under nitrogen atmosphere, a mixture of 0.74 g of t-butyl (1R)-trans-3-[(E)-3-(2-propenyloxyimino)-2-methyl-1-propenyl]-2,2-dimethylcyclopropanecarboxylate, catalytic amount of p-toluenesulfonic acid and 10 ml of toluene was stirred for 1 hour under reflux. The reaction mixture was cooled down to room temperature, then, concentrated under reduced pressure. The residue was subjected to silica gel column chromatography to obtain 0.47 g of (1R)-trans-3-[(E)-3-(2-propenyloxyimino)-2-methyl-1-propenyl]-2,2-dimethylcyclopropanecarboxylic acid:

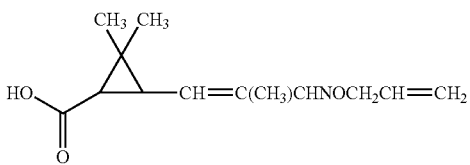

$^1$H-NMR (CDCl$_3$, TMS) δ (ppm): 7.69 (1H, s), 6.01 (1H, m), 5.40-5.19 (3H, m), 4.58 (2H, dt), 2.28 (1H, dd), 1.92 (3H, d), 1.61 (1H, d), 1.34 (3H, s), 1.20 (3H, s)

Reference Production Example 8

Under nitrogen atmosphere, a mixture of 1.0 g of t-butyl (1R)-trans-2,2-dimethyl-3-[(E)-2-methyl-3-oxo-1-propenyl]cyclopropanecarboxylate, 0.29 g of hydroxylamine hydrochloride, 5 ml of pyridine, 5 ml of water and 30 ml of 1,4-dioxane was stirred at room temperature for 3 hours. Ethyl acetate was added to the reaction mixture, and the mixture was washed with 1 mol/L hydrochloric acid and saturated brine respectively. The organic layer was dried over anhydrous magnesium sulfate, then, filtrated, and the filtrate was concentrated under reduced pressure. The residue was subjected to silica gel column chromatography to obtain 0.71 g of t-butyl (1R)-trans-3-[(E)-3-hydroxyimino-2-methyl-1-propenyl]-2,2-dimethylcyclopropanecarboxylate:

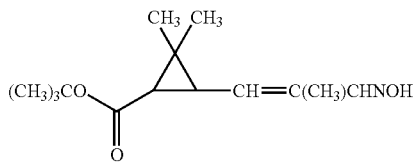

$^1$H-NMR (CDCl$_3$, TMS) δ (ppm): 7.70 (1H, s), 5.41 (1H, d), 2.16 (1H, dd), 1.91 (3H, d), 1.53 (1H, d), 1.46 (9H, s), 1.28 (3H, s), 1.17 (3H, s)

Reference Production Example 9

Under nitrogen atmosphere, to a mixture of 0.58 g of t-butyl (1R)-trans-3-[(E)-3-hydroxyimino-2-methyl-1-propenyl]-2,2-dimethylcyclopropanecarboxylate, 2.0 g of 1-iodopropane and 10 ml of anhydrous dimethylformamide (hereinafter, abbreviated as DMF) was added 0.10 g of sodium hydroxide (60% dispersion in mineral oil) and the mixture was stirred at room temperature overnight. Thereafter, 1 mol/L hydrochloric acid was added to the reaction mixture, and the mixture was extracted with ethyl acetate. The organic layer was washed with saturated brine, and dried over anhydrous magnesium sulfate, then, filtrated, and the filtrate was concentrated under reduced pressure. The residue was subjected to silica gel column chromatography to obtain 0.56 g of t-butyl (1R)-trans-2,2-dimethyl-3-[(E)-2-methyl-3-propoxyimino-1-propenyl]cyclopropanecarboxylate:

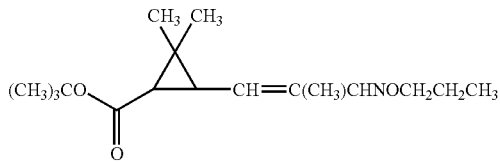

$^1$H-NMR (CDCl$_3$, TMS) δ (ppm): 7.66 (1H, s), 5.35 (1H, d), 4.02 (2H, t), 2.15 (1H, dd), 1.91 (3H, d), 1.72-1.63 (2H, m), 1.51 (1H, d), 1.46 (9H, s), 1.28 (3H, s), 1.15 (3H, s), 0.94 (3H, t)

Reference Production Example 10

Under nitrogen atmosphere, a mixture of 0.56 g of t-butyl (1R)-trans-2,2-dimethyl-3-[(E)-2-methyl-3-propoxyimino-1-propenyl]cyclopropanecarboxylate, catalytic amount of p-toluenesulfonic acid and 10 ml of toluene was stirred for 2 hours under reflux. The reaction temperature was cooled down to room temperature, then, concentrated under reduced pressure. The residue was subjected to silica gel column chromatography to obtain 0.25 g of t-butyl (1R)-trans-2,2-dimethyl-3-[(E)-2-methyl-3-propoxyimino-1-propenyl]cyclopropanecarboxylic acid:

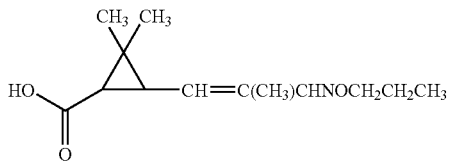

$^1$H-NMR (CDCl$_3$, TMS) δ (ppm): 7.66 (1H, s), 5.37 (1H, d), 4.02 (2H, t), 2.28 (1H, dd), 1.92 (3H, s), 1.73-1.63 (2H, m), 1.60 (1H, d), 1.34 (3H, s), 1.19 (3H, s), 0.94 (3H, t)

Reference Production Example 11

Under nitrogen atmosphere, a mixture of 0.30 g of methyl (1R)-trans-2,2-dimethyl-3-[(E)-2-methyl-3-oxo-1-propenyl]cyclopropanecarboxylate, 0.17 g of O-isopropylhydroxylamine hydrochloride and 2 ml of pyridine was stirred at room temperature for 6 hours. Then, ethyl acetate was added to the reaction mixture, and the mixture was washed with 1 mol/L hydrochloric acid and saturated brine respectively. The organic layer was dried over anhydrous magnesium sulfate, then, filtrated, and the filtrate was concentrated under reduced pressure. The residue was subjected to silica gel column chromatography to obtain 0.27 g of methyl (1R)-trans-3-[(E)-3-isopropoxyimino-2-methyl-1-propenyl]-2,2-dimethylcyclopropanecarboxylate:

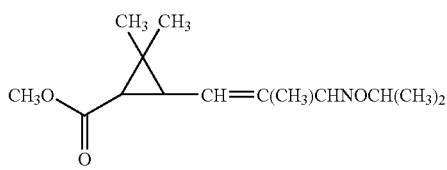

$^1$H-NMR (CDCl$_3$, TMS) δ (ppm): 7.63 (1H, s), 5.34 (1H, d), 4.34 (1H, m), 3.69 (3H, s), 2.25 (1H, dd), 1.92 (3H, d), 1.59 (1H, d), 1.30 (3H, s), 1.24 (6H, d), 1.17 (3H, s)

Reference Production Example 12

Under nitrogen atmosphere, a mixture of 0.27 g of methyl (1R)-trans-3-[(E)-3-isopropoxyimino-2-methyl-1-propenyl]-2,2-dimethylcyclopropanecarboxylate, 3.3 ml of 1 mol/L sodium hydroxide aqueous solution and 3.3 ml of methanol was stirred at 60° C. for 4.5 hours. Then, water was added to the reaction mixture, and the mixture was washed with diethyl ether. 1 mol/L hydrochloric acid was added to the resultant aqueous layer to make the layer acidic, and the mixture was extracted with diethyl ether, then, the organic layer was dried over anhydrous magnesium sulfate, then, filtrated. The filtrate was concentrated under reduced pressure, to obtain 0.25 g of a crude product of (1R)-trans-3-[(E)-3-isopropoxyimino-2-methyl-1-propenyl]-2,2-dimethylcyclopropanecarboxylic acid:

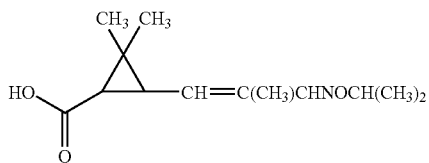

The product was subjected to Production Example 5 without purification.

Reference Production Example 13

Under nitrogen atmosphere, to a mixture of 0.58 g of t-butyl (1R)-trans-3-[(E)-3-hydroxyimino-2-methyl-1-propenyl]-2,2-dimethylcyclopropanecarboxylate, 0.75 g of 3-chloropropyne and 10 ml of anhydrous DMF was added 88 mg of sodium hydride (60% dispersion in mineral oil), and the mixture was stirred at room temperature overnight. Then, 1 mol/L hydrochloric acid was added to the reaction mixture, and the mixture was extracted with ethyl acetate. The organic layer was washed with saturated brine, dried over anhydrous magnesium sulfate, then, filtrated, and the filtrate was concentrated under reduced pressure. The residue was subjected to silica gel column chromatography to obtain 0.46 g of t-butyl (1R)-trans-2,2-dimethyl-3-[(E)-2-methyl-3-(2-propynyloxyimino)-1-propenyl]cyclopropanecarboxylate:

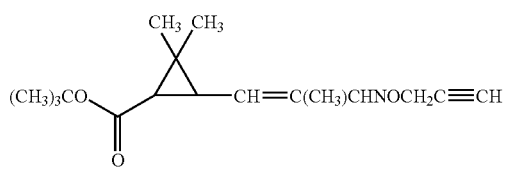

$^1$H-NMR (CDCl$_3$, TMS) δ (ppm): 7.69 (1H, s), 5.40 (1H, d), 4.67 (2H, d), 2.46 (1H, t), 2.16 (1H, dd), 1.92 (3H, d), 1.53 (1H, d), 1.46 (9H, s), 1.28 (3H, s), 1.16 (3H, s)

Reference Production Example 14

Under nitrogen atmosphere, a mixture of 0.46 g of t-butyl (1R)-trans-2,2-dimethyl-3-[(E)-2-methyl-3-(2-propynyloxyimino)-1-propenyl]cyclopropanecarboxylate, catalytic amount of p-toluenesulfonic acid and 10 ml of toluene was stirred for 3.5 hours under reflux. The reaction mixture was cooled down to room temperature, then, the mixture was concentrated under reduced pressure. The residue was subjected to silica gel column chromatography to obtain 0.35 g of (1R)-trans-2,2-dimethyl-3-[(E)-2-methyl-3-(2-propynyloxyimino)-1-propenyl]cyclopropanecarboxylic acid:

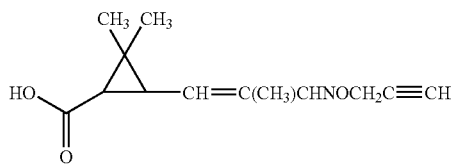

$^1$H-NMR (CDCl$_3$, TMS) δ (ppm): 7.69 (1H, s), 5.42 (1H, d), 4.68 (2H, d), 2.47 (1H, t), 2.28 (1H, dd), 1.93 (3H, d), 1.62 (1H, d), 1.35 (3H, s), 1.20 (3H, s)

Next, Formulation Examples will be described. Parts are by weight.

Formulation Example 1

To a solution of 20 parts of any one of the present compounds (1) to (6) in 65 parts of xylene is added 15 parts of Sorpol 3005X (registered trademark of Toho Chemical Industry Co., LTD.), and the mixture is thoroughly mixed with stirring to obtain an emulsifiable concentrate.

Formulation Example 2

To 40 parts of any one of the present compounds (1) to (6) is added 5 parts of Sorpol 3005X, and the mixture is thoroughly mixed with stirring. To the mixture are added 32 parts of Carplex #80 (synthetic hydrated silica, registered trademark of Shionogi & Co., Ltd.) and 23 parts of 300-mesh diatomaceous earth, and the resulting mixture is thoroughly mixed with a juice mixer to obtain a wettable powder.

Formulation Example 3

A mixture of 1.5 parts of any one of the present compounds (1) to (6), 1 part of Tokusil GUN (synthetic hydrated silica, manufactured by Tokuyama Corp.), 2 parts of Reax 85A (sodium ligninsulfonate, manufactured by West vaco chemicals), 30 parts of Bentonite Fuji (bentonite, manufactured by Hojun Co.) and 65.5 parts of Shokozan A clay (kaolin clay, manufactured by Shokozan Kogyosho Co.) is thoroughly pulverized. To the resulting mixture is added water, and the mixture is kneaded, granulated with a piston-granulator and dried to obtain a 1.5% granule.

Formulation Example 4

A mixture of 10 parts of any one of the present compounds (1) to (6), 10 parts of phenylxylylethane and 0.5 part of Sumidur L-75 (tolylenediisocyanate manufactured by Sumika Bayer Urethane Co., Ltd.) is added to 20 parts of 10% aqueous solution of gum arabic, and stirred with a homomixer to obtain an emulsion having a mean particle diameter of 20 µm. To this is added 2 parts of ethylene glycol, and stirred for 24 hours on a water bath at 60° C. to obtain microcapsule slurry. On the other hand, 0.2 part of xanthan gum and 1.0 part of Veegum R (aluminum magnesium silicate manufactured by Sanyo Chemical Co., Ltd.) are dispersed in 56.3 parts of ion-exchanged water to obtain a thickener solution. Mixing of 42.5 parts of the above microcapsule slurry and 57.5 parts of the thickener solution provides a microencapsulated formulation.

Formulation Example 5

A mixture of 10 parts of any one of the present compounds (1) to (6) and 10 parts of phenylxylylethane is added to 20 parts of 10% aqueous solution of polyethylene glycol, and the mixture is stirred with a homomixer to obtain an emulsion having a mean particle diameter of 3 µm. On the other hand, 0.2 part of xanthan gum and 1.0 part of Veegum R (aluminum magnesium silicate manufactured by Sanyo Chemical Co., Ltd.) are dispersed in 58.8 parts of ion-exchanged water to give a thickener solution. Mixing of 40 parts of the above emulsion and 60 parts of the thickener solution provides a flowable formulation.

Formulation Example 6

A mixture of 5 parts of any one of the present compounds (1) to (6), 3 parts of Carplex #80 (fine powder of synthetic hydrated silicon dioxide, trademark of Shionogi & Co., Ltd.), 0.3 part of PAP (mixture of monoisopropyl phosphate and diisopropyl phosphate) and 91.7 parts of 300-mesh talc are stirred with a juice mixer to obtain a dust.

Formulation Example 7

A solution of 0.1 part of any one of the present compounds (1) to (6) in 10 parts of dichloromethane is mixed with 89.9 parts of deodorized kerosene to obtain an oil solution.

Formulation Example 8

A solution of 1 part of any one of the present compounds (1) to (6), 5 parts of dichloromethane and 34 parts of deodorized kerosene is filled in an aerosol vessel. A valve is attached to the vessel and 60 parts propellant (liquefied petroleum gas) is charged under pressure through the valve to obtain an oily aerosol.

Formulation Example 9

A solution of 0.6 part of any one of the present compounds (1) to (6), 5 parts of xylene, 3.4 parts of deodorized kerosene and 1 part of Atmos 300 (emulsifier, trademark of Atlas Chemical Co.) and 50 parts of water are filled in an aerosol vessel. A valve is attached to the vessel and 40 parts propellant (liquefied petroleum gas) is charged under pressure through the valve to obtain an aqueous aerosol.

Formulation Example 10

A solution of 0.3 g of any one of the present compounds (1) to (6) in 20 ml of acetone is uniformly mixed with 99.7 g of a base material for a mosquito-coil (mixture of Tabu powder, *Pyrethrum marc* and wood powder at the ratio of 4:3:3). To the mixture is added 100 ml of water and the resulting mixture is thoroughly kneaded, then molded and dried to obtain a mosquito-coil.

Formulation Example 11

A solution is prepared by adding acetone to 0.8 g of any one of the present compounds (1) to (6) and 0.4 g of piperonyl butoxide and adjusting to 10 ml. A base material (a plate of compacted fibrils of a mixture of pulp and cotton linter: 2.5 cm×1.5 cm, 0.3 cm of thickness) is uniformly impregnated with 0.5 ml of the above solution to obtain a mosquito-mat for electric heating.

Formulation Example 12

A solution of 3 parts of any one of the present compounds (1) to (6) in 97 parts of deodorized kerosene is filled in a container made of polyvinyl chloride. Into the container is inserted an absorptive wick made of inorganic powder solidified with a binder and then calcined, whose upper portion can be heated with a heater, to obtain a part of a absorptive wick type electric heating fumigation device.

Formulation Example 13

A porous ceramic plate (4.0 cm×4.0 cm, 1.2 cm of thickness) is impregnated with a solution of 100 mg of any one of the present compounds (1) to (6) in an appropriate amount of acetone to obtain a fumigant for heating.

Formulation Example 14

A solution of 100 µg of any one of the present compounds (1) to (6) in an appropriate amount of acetone is uniformly applied on a filter paper strip (2.0 cm×2.0 cm, 0.3 mm of thickness). Then, acetone is vaporized to obtain a volatile agent for using at room temperature.

The following Test Examples will show that the present compound is useful as an active ingredient for pest controlling agents.

Test Example 1

The formulation of the sample compound obtained in Formulation Example 7 was diluted with dichloromethane/deodorized kerosene=1/9 mixed solution so that the active ingredient concentration was 0.025%, to prepare a test solution.

Ten adult houseflies (5 males and 5 females) were left and bred in a polyethylene cup (bottom diameter: 10.6 cm) which was then capped with 16-mesh nylon gauze. The polyethylene cup was placed on the bottom of a test chamber (46 cm×46 cm, height: 70 cm). From a height of 30 cm above the upper surface of the polyethylene cup, 0.5 ml of the test solution was sprayed using a spray gun at a spraying pressure of 0.9 kg/cm². Immediately after spraying, the cup was taken out from the test container, and two minutes after, the number of knocked-down insects was counted (repeated twice).

As a result, in treatments with the present compounds (1), (2), (3), (4), (5) and (6), the knock down ratio of sample insects was 70% or more (repeated twice).

Test Example 2

The formulation of the sample compound obtained in Formulation Example 7 was diluted with dichloromethane/deodorized kerosene=1/9 mixed solution so that the active ingredient concentration was 0.00625%, to prepare a test solution.

Ten adult houseflies (4 or 5 males and 4 or 5 females each) were left in a cubic glass chamber (70 cm at each side), and 0.7 ml of the test solution was sprayed through a small window at the side of the chamber using a spray gun at a spraying pressure of 0.9 kg/cm². 10 minutes after spraying, the number of knocked-down insects was counted (repeated twice).

As a result, in treatment with the present compound (1), the knock down ratio of sample insects was 100% (repeated twice).

The same test as described above was carried out using, as a control, 2,5-dioxo-3-(2-propynyl)imidazolidine-1-ylmethyl (1R)-trans-2,2-dimethyl-3-(2-methyl-1-propenyl)cyclopropane carboxylate:

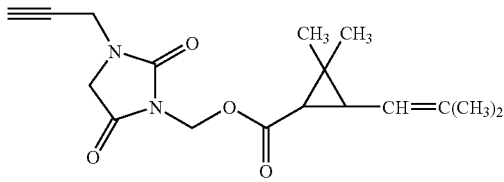

(A)

(hereinafter, referred to as comparative compound (A)) described in U.S. Pat. No. 4,176,189 as Present Compound (7), instead of the present compound (1).

As a result, in treatment with the comparative compound (A), the knock down ratio of sample insects was 42% (repeated twice).

Test Example 3

The formulation of the sample compound obtained in Formulation Example 7 was diluted with dichloromethane/deodorized kerosene=1/9 mixed solution so that the active ingredient concentration was 0.00625%, to prepare a test medicinal solution.

A container (8.75 cm in diameter, 7.5 cm in height, bottom covered 16-mesh iron net and inside wall painted butter for preventing tested pill bugs to escape) having 10 German cockroach (5 males and 5 females, *Blattella germanica*) therein was set on the bottom of a test chamber (46 cm×46 cm, height: 70 cm). From a height of 60 cm above the upper surface of the container, 1.5 ml of the test solution was sprayed using a spray gun at a spraying pressure of 0.4 kg/cm². After 30 seconds, the German cockroach were taken out and put into a clean plastic cup having 8.2 cm in diameter. The lid having holes was covered on the cup. 1 minutes after spraying, the number of knocked-down insects was counted (repeated twice).

As a result, in treatment with the present compound (1), the knock down ratio of sample insects was 100% (repeated twice).

The same test as described above was carried out using, as a control, 5-(2-propynyl)furan-2-ylmethyl (1R)-trans-3-[(E)-3-methoxyimino-2-methyl-1-propenyl]-2,2-dimethylcyclopropanecarboxylate:

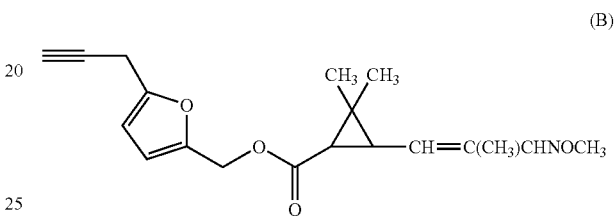

(B)

(hereinafter, referred to as comparative compound (B)) described in JP A S51-125739 as Present Compound (9), instead of the present compound (1).

As a result, in treatment with the comparative compound (B), the knock down ratio of sample insects was 0% (repeated twice).

INDUSTRIAL APPLICABILITY

The present compound is useful as an active ingredient for a pest controlling agent.

The invention claimed is:

1. An ester compound represented by the formula (I):

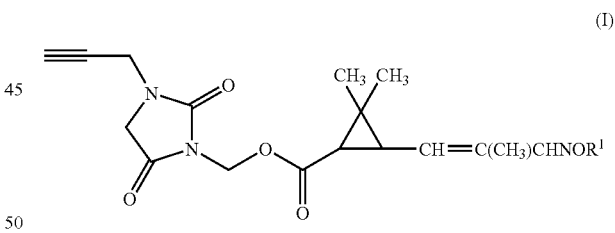

(I)

wherein, $R^1$ represents a C1-C3 alkyl group, a 2-propenyl group or a 2-propynyl group.

2. The ester compound according to claim 1, wherein $R^1$ is a C1-C3 alkyl group.

3. A pest controlling agent comprising the ester compound according to claim 1 as an active ingredient.

4. A method for controlling pests comprising applying an effective amount of the ester compound according to claim 1 to the pests or a place where the pests inhabit.

5. A pest controlling agent comprising the ester compound according to claim 2 as an active ingredient.

6. A method for controlling pests comprising applying an effective amount of the ester compound according to claim 2 to the pests or a place where the pests inhabit.

7. The ester compound according to claim 1, wherein $R^1$ is a 2-propenyl group.

8. A pest controlling agent comprising the ester compound according to claim 7 as an active ingredient.

9. A method for controlling pests comprising applying an effective amount of the ester compound according to claim 7 to the pests or a place where the pests inhabit.

10. The ester compound according to claim 1, wherein $R^1$ is 2-propynyl group.

11. A pest controlling agent comprising the ester compound according to claim 10 as an active ingredient.

12. A method for controlling pests comprising applying an effective amount of the ester compound according to claim 10 to the pests or a place where the pests inhabit.

* * * * *